(12) United States Patent  
Cimino

(10) Patent No.: US 8,298,163 B1
(45) Date of Patent: Oct. 30, 2012

(54) NON-INVASIVE ULTRASONIC SOFT-TISSUE TREATMENT APPARATUS

(75) Inventor: William W. Cimino, Louisville, CO (US)

(73) Assignee: Body Beam Research Inc., Louisville, CO (US)

( * ) Notice: Subject to any disclaimer, the term of this patent is extended or adjusted under 35 U.S.C. 154(b) by 145 days.

(21) Appl. No.: 12/771,820

(22) Filed: Apr. 30, 2010

Related U.S. Application Data

(63) Continuation of application No. 12/687,234, filed on Jan. 14, 2010, now abandoned.

(60) Provisional application No. 61/174,554, filed on May 1, 2009.

(51) Int. Cl.
*A61H 1/00* (2006.01)

(52) U.S. Cl. .......................................................... 601/3

(58) Field of Classification Search .................. 601/3
See application file for complete search history.

(56) References Cited

U.S. PATENT DOCUMENTS

| | | | |
|---|---|---|---|
| 4,315,514 A | 2/1982 | Drewes et al. | |
| 4,718,421 A * | 1/1988 | Rohwedder et al. | 601/4 |
| 5,054,470 A | 10/1991 | Fry et al. | |
| 5,143,063 A | 9/1992 | Fellner | |
| 5,180,363 A * | 1/1993 | Idemoto et al. | 604/22 |
| 5,209,221 A | 5/1993 | Riedlinger | |
| 5,402,792 A | 4/1995 | Kimura | |
| 5,507,790 A | 4/1996 | Weiss | |
| 5,665,053 A | 9/1997 | Jacobs | |
| 5,827,204 A | 10/1998 | Grandia et al. | |
| 5,884,631 A | 3/1999 | Silberg | |
| 6,071,239 A | 6/2000 | Cribbs et al. | |
| 6,350,245 B1 * | 2/2002 | Cimino | 601/2 |
| 6,443,914 B1 | 9/2002 | Costantino | |
| 6,450,979 B1 | 9/2002 | Miwa et al. | |
| 6,500,141 B1 | 12/2002 | Irion et al. | |
| 6,607,498 B2 | 8/2003 | Eshel | |
| 6,626,854 B2 | 9/2003 | Friedman et al. | |
| 6,645,162 B2 | 11/2003 | Friedman et al. | |
| 6,645,229 B2 | 11/2003 | Matsumura et al. | |
| 6,725,095 B2 | 4/2004 | Fenn et al. | |
| 6,821,274 B2 | 11/2004 | McHale et al. | |
| 7,258,674 B2 | 8/2007 | Cribbs et al. | |
| 7,331,951 B2 | 2/2008 | Eshel et al. | |
| 7,347,855 B2 | 3/2008 | Eshel et al. | |
| 2004/0039312 A1 | 2/2004 | Hillstead et al. | |
| 2004/0210214 A1 | 10/2004 | Knowlton | |
| 2004/0215110 A1 | 10/2004 | Kreindel | |
| 2005/0154314 A1 | 7/2005 | Quistgaard | |
| 2005/0154431 A1 | 7/2005 | Quistgaard et al. | |
| 2005/0187495 A1 | 8/2005 | Quistgaard et al. | |
| 2005/0193451 A1 | 9/2005 | Quistgaard et al. | |
| 2005/0261584 A1 | 11/2005 | Eshel et al. | |
| 2006/0058707 A1 | 3/2006 | Barthe et al. | |
| 2006/0122509 A1 | 6/2006 | Desilets | |
| 2007/0055156 A1 | 3/2007 | Desilets et al. | |
| 2007/0239075 A1 * | 10/2007 | Rosenberg et al. | 601/2 |
| 2007/0239077 A1 | 10/2007 | Azhari et al. | |
| 2008/0097253 A1 | 4/2008 | Pedersen et al. | |
| 2008/0255478 A1 * | 10/2008 | Burdette | 601/2 |

* cited by examiner

*Primary Examiner* — Tse Chen
*Assistant Examiner* — Hien Nguyen
(74) *Attorney, Agent, or Firm* — Marsh Fischmann & Breyfogle LLP

(57) ABSTRACT

Non-invasive apparatus and methods are disclosed for treatment of soft-tissues of a human or animal body, and, more particularly, non-invasive treatment apparatus and methods for destruction of adipose tissues of a patient using focused delivery of ultrasonic energy in a group of focal zones.

20 Claims, 8 Drawing Sheets

NON-INVASIVE ULTRASONIC SOFT-TISSUE TREATMENT APPARATUS

CROSS-REFERENCE TO RELATED APPLICATION

This application claims a priority benefit under 35 U.S.C. §119(e) to U.S. Provisional Patent Application No. 61/174,554 entitled "NON-INVASIVE ULTRASONIC SOFT-TISSUE TREATMENT APPARATUS AND METHOD" filed May 1, 2009, each and every portion of which is incorporated herein by reference as if it were set forth herein in full. This application is a continuation of co-pending U.S. patent application Ser. No. 12/687,234 entitled "NON-INVASIVE ULTRASONIC SOFT-TISSUE TREATMENT APPARATUS" filed Jan. 14, 2010, each and every portion of which is incorporated herein by reference as if it were set forth herein in full.

STATEMENT REGARDING FEDERALLY SPONSORED RESEARCH

Not Applicable

REFERENCE TO A MICROFICHE APPENDIX

Not Applicable

FIELD OF THE INVENTION

This invention relates generally to apparatus and methods for non-invasive treatment of soft-tissues of a human or animal body, and, in a particular application, for treatment to destroy adipose tissue using focused delivery of ultrasonic energy.

BACKGROUND OF THE INVENTION

Liposuction is an invasive surgical procedure for altering the human form, specifically by removal of localized deposits of fatty tissues that are unresponsive to diet or exercise. The procedure is also known as suction lipectomy, lipolysis, and more recently as body contouring surgery, body sculpting surgery, or suction-assisted liposuction. It is most often performed by plastic surgeons, although dermatologists, gynecologists, and other surgical specialties also perform the procedure.

The liposuction procedure is typically accomplished by inserting a small liposuction cannula through an incision in the skin, applying a suction source to the end of the liposuction cannula that remains outside of the body, and forcing the working end of the liposuction cannula forward and backward in the layer of fatty tissue. The fatty tissue is torn, crushed, or avulsed, and is then aspirated through small openings along the sides of the liposuction cannula near the tip and then through a central lumen in the liposuction cannula to a tissue canister placed in-line with the liposuction cannula and the suction source. The procedure may involve multiple incisions and many passes of the liposuction cannula in each incision to achieve the desired cosmetic effect for the patient.

The liposuction procedure can be traumatic for the patient. The liposuction cannula does not discriminate between adipose tissue and other tissues such as nerves, blood vessels, or lymph tissues. The mechanical disruption of these tissues by the liposuction cannula may result in, among other things, bleeding, bruising, temporary numbness, pain, hyperpigmentation of the skin, or swelling. Complications may include infection, skin loss, or seroma formation. Patients generally have a post-operative course of healing that may range from about a week to several weeks or even a few months depending on the volume of adipose tissue removed. The final cosmetic result achieved for the patient is a function of the skill of the surgeon, the particular attributes of a patient, and the type of surgical instrumentation used in the surgery. A liposuction procedure may result in a less than uniform or smooth removal of adipose tissue, resulting in shape or skin contour irregularities and a final cosmetic result for the patient that is less than desirable.

Therefore, there has been a need to improve on the instrumentation and methods of liposuction for body contouring so that less damage would be done to the soft-tissues such as blood vessels, nerves, lymph tissue, and connective tissue while reducing the amount or number of adipose cells in a targeted area. Further, there has been a need to improve on the instrumentation and methods of liposuction for body contouring so that the there would be reduced risk of bleeding, bruising, pain, swelling, and other surgically related sequalae. Still further, there has been a need to improve on the instrumentation and methods of liposuction for body contouring so that adipose tissue could be sculpted in a more uniform and predictable manner so that an improved and more predictable cosmetic result could be achieved for the patient.

Recently, several instruments have combined ultrasonic vibrations and a liposuction cannula to improve upon the tissue discrimination capability of the liposuction cannula and to provide an instrument that removes adipose tissue more uniformly than prior liposuction cannulae. This technique is commonly referred to as ultrasound-assisted lipoplasty. Ultrasound-assisted lipoplasty is also an invasive surgical procedure, requiring an incision in the skin to insert the ultrasonically vibrating cannulae or probe. In a typical ultrasound-assisted lipoplasty procedure, an ultrasonically vibrating cannula or probe is inserted through an incision in the patient's skin and passed forward and backward through the adipose tissue layer, directly contacting the tissues to be treated. The ultrasonically vibrating cannula or probe fragments or emulsifies the adipose tissues, which are then usually aspirated either through a central lumen in the ultrasonically vibrating cannula or in a separate sequential step using an aspiration cannula. This approach is still an invasive surgical approach to body contouring surgery and therefore still suffers from similar post-surgical consequences and potential complications described above for the liposuction procedure.

The use of non-invasive (non-surgical) ultrasound for medical purposes has long been known, specifically for diagnostic imaging where the frequency and the ability to focus the ultrasonic beam determine the imaging resolution of the system. Diagnostic imaging systems typically operate at frequencies between 1 MHz and 30 MHz to achieve the desired imaging resolution, and operate at very low ultrasonic powers to minimize any potential damage to tissues. Diagnostic ultrasound is non-invasive, meaning that no incisions in the skin are required.

Focused ultrasound with sufficient ultrasonic power to fragment or otherwise destroy adipose tissue provides a non-invasive method of body contouring. An appropriately designed system focuses the ultrasonic energy at the depth of the targeted fatty tissue and has a significantly reduced energy density both above and below the focal zone, as well as lateral to the focal zone, thereby preserving the tissues above and below the focal zone. The benefits of a non-invasive body contouring method, compared to invasive (surgical) methods are: 1) a potentially shorter treatment time for the patient because a surgical operating room setup is not required; 2)

increased safety because surgical trauma is eliminated and anesthesia is not required (general anesthesia, IV sedation, or injected local anesthetic); and 3) reduced recovery time and reduced post-operative pain. The primary limitations of a non-invasive focused ultrasound approach to body contouring, compared to invasive (surgical) methods, are: 1) less tissue can be treated in a single session, thereby requiring multiple treatments to achieve a desired body contour, and 2) results do not appear immediately, but rather over time as the body resorbs and processes destroyed adipose tissue.

Many patents disclose for the non-invasive use of ultrasound to heat soft-tissues of a patient, or to create cavitation within the soft-tissues of a patient, or to lyse or otherwise destroy fatty/adipose tissue. U.S. Pat. No. 5,143,063 to Fellner (1992) has a method for non-invasively eliminating excess healthy adipose tissue in the subcutaneous layer in humans, the method having steps of selecting a site on the body with excess fatty tissue to be eliminated; focusing radiant energy on the cells in the site to raise the temperature; and maintaining the radiant energy focused at the site until the adipose tissue at the site absorbs enough energy to cause cell destruction. U.S. Pat. No. 6,626,854 to Friedman (2003) has a system for destroying subcutaneous tissue with a transducer producing focused acoustic energy along a linear focal zone that is parallel to the plane of the tissue, drive circuitry, a controller for controlling the drive circuitry with a duty cycle of about 20% to minimize heating. U.S. Pat. No. 6,350,245 to Cimino (2002) has a hand-held ultrasonic device for fragmenting/emulsifying a volume of tissue below the skin with a focusing lens in the frequency range 100-250 kHz. U.S. Pat. No. 6,071,239 to Cribbs (2000) has a method of destroying fat cells in the subcutaneous layer with an ultrasonic transducer array with the beam focused in multiple discrete focal zones where the discrete focal zones are spaced sufficiently to preserve the structural integrity of the tissue. U.S. Pat. No. 6,443,914 to Constantino (2002) has a method of treating cellulite by application of ultrasound energy to cause damage to normal cells to reinforce a layer of connective tissue. U.S. Pat. No. 7,347,855 to Eshel (2008) has a method and apparatus for lysing adipose tissue using focused ultrasonic energy with a modulator that modulates the ultrasonic energy so most of the adipose tissue is lysed and the non-adipose tissue is not lysed. U.S. Pat. No. 6,607,498 to Eshel (2003) has a method and apparatus for lysing adipose tissue by applying an ultrasonic transducer to the skin of the patient and focusing the ultrasonic energy on the adipose tissue; electrically activating the ultrasonic transducer to transmit periodic waves sufficient to cause cavitation and lysis of the adipose tissue without damaging adjacent non-adipose tissue. U.S. Pat. No. 5,209,221 to Riedlinger (1993) has an ultrasonic system to treat pathological tissue by producing cavitation with a frequency greater than 20 kHz with a means to generate pulses, and a means to focus. U.S. Pat. No. 5,054,470 to Fry (1991) has an ultrasound treatment transducer with a focused beam, a flat PZT transducer plate, an acoustic coupling medium, a first pressurizing means and an air pressure means. U.S. Pat. No. 5,402,792 to Kimura (1995) has an ultrasonic apparatus with a wave emitting surface where the wave emitting surface has a plurality of different radii of curvature and different centers of concavity. U.S. Pat. No. 5,827,204 to Grandia (1998) has an apparatus for affecting tissue with low-frequency ultrasound and a means of superimposing a high frequency ultrasound signal to cause the amplitude to exceed the cavitation threshold. U.S. Pat. No. 4,315,514 to Drewes (1982) has a method of destroying selected cells by selecting a transmission path, determining a resonant frequency of the cells, comparing the transmissibility of the cells to the resonant frequency, selecting a destructive frequency, and transmitting energy at the destructive frequency. U.S. Pat. No. 5,507,790 to Weiss (1996) has a method of transdermally increasing the rate of lipolysis for body contour modification by focusing radiant energy (including ultrasonic energy with a focusing lens) on the target site to raise the temperature and cause the release of free fatty acids, thus reducing the volume of the fat cells.

These prior approaches have to varying degrees addressed issues relating to treatment efficacy and safety. But in many instances the approaches involve complex equipment and/or procedures that complicate the job of medical practitioners attempting to perform treatments. Moreover, damage to surrounding, non-targeted tissue remains a concern. There remains a need unmet by these prior approaches for non-invasive treatment methods and equipment that are safe and effective for treating targeted tissue while minimizing potential for damage to surrounding, non-targeted tissue, and that also are easy for individual medical practitioners to use to quickly perform a treatment.

SUMMARY OF THE INVENTION

The invention provides apparatus and methods for non-invasive treatment of soft-tissue involving multiple simultaneously operating, geometrically focused beams of ultrasonic energy generated at a resonant frequency in a range of from 275 KHz to 800 KHz, with at least portions of individual focal zones of the geometrically focused beams coinciding to form a group focal zone with high energy density, the group focal zone which is positioned during a treatment operation within soft-tissue located within a depth range of from about 0.5 centimeter to 10 centimeters, and often within an even narrower depth range, below the surface of the skin of the patient. In preferred implementations, the soft-tissue to be treated is adipose tissue. Treatment of the soft-tissue involves destruction of at least a portion of the soft-tissue, which may be accomplished primarily due to positive and negative pressure effects within the tissue. Although the positive and negative pressures generated during a treatment may induce cavitation in the soft-tissues, in a preferred implementation cavitation is minimized. Treatment times for effective treatment may be kept short. Tissue destruction due to elevated temperature caused by thermal effects in the tissue may largely be avoided, along with the potential for thermal damage to surrounding tissue that is not targeted for treatment. Moreover, the treatments may be performed in an uncomplicated manner and with an easy-to-use, hand-held apparatus with an uncomplicated design.

The ability to focus an ultrasonic beam is directly related to the wavelength of the selected frequency in tissue. The focal length of an acoustic lens refers to the distance from the lens to the center of the focal zone corresponding to the lens, as measured along the focal axis. At 20 kHz the wavelength in tissue is approximately 7.5 centimeters, fundamentally limiting the focal length of an acoustic lens to a minimum of about 50-60 centimeters, using a single geometrically focused lens. (This calculation assumes a minimum lens diameter of 5 times the wavelength and a focal length to lens diameter ratio of 1.5.) Such a focal length is too long for effective treatment of adipose tissue, which is often located at a depth of approximately 0.5 to 5 centimeters below the skin, although in some cases adipose tissue may extend to as deep as 10 centimeters below the skin. Thus, at lower ultrasonic frequencies the ability to geometrically focus at depths appropriate for adipose tissue is not physically possible. The lower frequency limit is not precisely defined but can be defined for practical purposes to be in a range from 150 kHz to 250 kHz. Below this frequency range practical focusing at depths appropriate for adipose tissue is not possible using geometrically focused lenses. A low-frequency ultrasonic transducer with a long focal length could be spaced from the skin layer such that the focal zone is in targeted tissues at shallow depths of 0.5 to 5 centimeters below the skin. However, the depth of focus (different than the focal length of the lens), which is the length of the focal zone measured along the focal axis, is also too long to be useful at these lower frequencies. A long depth of focus has a high potential to include within the focal zone tissue above (e.g., skin) and/or below the tissue targeted for treatment. This could, for example cause heating and pain in the skin layer. Similar concerns exist for the deeper tissue, which may be unnecessarily heated or damaged by a long depth of focus. Thus, it is not practical to use geometric focusing according to the approach of the invention at those lower ultrasonic frequencies, generally below 250 kHz, and especially when targeting tissues at shallow depths within 5 centimeters below the skin.

As the frequency of ultrasonic energy is increased the ability to geometrically focus the ultrasonic energy with smaller focal lengths and with a shorter depth of focus is improved. At 1 MHz the wavelength in soft-tissue is approximately 0.15 centimeters, and a focal length in the 1 to 5 centimeter range can be achieved. While it is possible to achieve appropriate focal lengths and with appropriate depth of focus at the higher ultrasonic frequencies, such as 1 MHz and above, the majority of ultrasonic power at these higher frequencies is absorbed in the tissue in the form of heat, creating a thermal injury to tissues if the power density is large enough. The primary interaction between the ultrasonic energy and the tissue at these higher frequencies, with sufficient power density, is heating, due to the increasing absorption of the ultrasonic energy as a function of frequency. Heat, causing a thermal injury, is not tissue specific, thus all tissues in the focal zone will be heated and damaged, not preferentially adipose cells. Heating of the soft-tissues is significantly reduced as the ultrasonic frequency is reduced due to lower absorption of the ultrasonic energy by the soft-tissues as a function of frequency.

As the ultrasonic frequency is lowered the primary interaction of the ultrasonic energy with the soft-tissue becomes dominated by positive and negative pressure effects and potentially cavitation effects, rather than a predominantly thermal effect. One object of the invention is to provide a treatment apparatus able to focus ultrasonic energy at lower ultrasonic frequencies to minimize thermal effects in the tissues while supplying sufficient ultrasonic power and control of the size and shape of the focal zone so that the desired tissue destruction is safely obtained.

In one aspect, the invention provides an apparatus, or device, for non-invasive ultrasonic treatment of subcutaneous soft-tissue of the body of a human or other mammalian subject, or patient. The apparatus includes two or more simultaneously operable acoustic assemblies retained in fixed relation to each other. The apparatus is electrically powered and is operable when connected to an appropriate electrical power source to energize the acoustic assemblies to simultaneously generate ultrasonic energy from each acoustic assembly. Each acoustic assembly generates ultrasonic energy at a selected resonant frequency in a range of 275 KHz to 800 KHz, with the ultrasonic energy generated by each acoustic assembly being geometrically focused in an individual focal zone located distal to the respective acoustic assembly. In one implementation, each acoustic assembly includes an acoustic lens oriented to provide the desired geometric focus to the ultrasonic energy generated by the acoustic assembly, thereby concentrating the ultrasonic energy from the acoustic assembly in the respective individual focal zone. The acoustic assemblies are oriented so that at least a portion of each individual focal zone spatially coincides (i.e., in intersecting portions of the respective ultrasonic beams) in a group focal zone, where the ultrasonic energies of the different acoustic assemblies are additive, or summing. By additive, or summing, it means that the ultrasonic energies of the different acoustic assemblies are such that the amplitudes of the ultrasonic energies combine to produce a combined ultrasonic energy within the group focal zone having a larger amplitude of vibration (i.e., higher energy) than the amplitude contribution from the ultrasonic energy from any one of the acoustic assemblies. In a preferred implementation, the acoustic assemblies operate at substantially the same resonant frequency and more preferably with the ultrasonic energies from each of the acoustic assemblies being substantially in phase with the ultrasonic energy from each other of the acoustic assemblies. Particularly preferred is for the acoustic assemblies to be oriented, focused and operated such that at least portions, and preferably substantially all, of the areas of highest concentrated energies in the individual focal zones of the acoustic assemblies coincide within the group focal zone. The apparatus must include at least two (2) of the acoustic assemblies, and preferably at least three (3) of the acoustic assemblies, but the apparatus may include any larger number of acoustic assembles. Typically, the apparatus includes a number of acoustic assemblies in a range having a lower limit selected from the group consisting of two (2), three (3) or four (4) and an upper limit selected from the group consisting of eight (8) and six (6). Preferred implementations are for the apparatus to include either three (3) or four (4) of the acoustic assemblies.

The group focal zone aspect of the invention provides a number of advantages from safety and treatment efficacy perspectives. One advantage is that the device may be designed so that the energies of the individual beams of ultrasonic energies are not sufficient by themselves to cause substantial damage to the soft-tissue, but with the combined energy in the group focal zone being sufficient to cause such substantial damage to the soft-tissue. This substantially reduces the potential for damage to tissue through which the individual ultrasonic energy beams pass before entering or after leaving the group focal zone. Also, the high energy density of the ultrasonic energy that it is possible to provide in the group focal zone, due to the combined energies of the individual ultrasonic beams, may be large enough that an effective treatment of soft-tissue within the group focal zone may be accomplished in a very short amount of time. A short treatment duration is of benefit to the medical practitioners performing treatments and to patients undergoing such treatments. Also, maintaining a short treatment time significantly reduces the potential for generation of significant thermal effects in treated tissue or surrounding tissue. Another major advantage of the group focal zone aspect of the invention is that the depth of the group focal zone below the surface of the skin can be adjusted to provide treatment at different depths, thereby treating different levels of adipose tissue. Treatment at different depths provides an improved ability to sculpt the tissue and also increases the volume of tissue treated. In the preferred method, treatment at a first depth is completed at one treatment time, and treatments at other depths are completed at other treatment times.

The group focal zone is considerably different from and should not be confused with the scanning effect a phased array of ultrasonic transducers. The scanning effect of a phase array involves a moving interference pattern between advancing ultrasonic wave fronts emanating from the timed firing of ultrasonic transducers in an array. A phased array does not involve a summing of the ultrasonic energies of the individual ultrasonic transducers as described herein. Moreover, the group focal zone of the present invention is fixed and stationary in relation to the ultrasonic assemblies of the apparatus that generate the geometrically focused beams, the overlap of which forms the group focal zone. This is significantly different than the moving front produced by a phased array that may be moved in a scanning fashion relative to the location of the ultrasonic transducers of the phase array. Moreover, the ultrasonic energy in a phased array is not geometrically focused.

The apparatus also includes an acoustic pad having an ultrasonic emission surface through which at least a portion of the ultrasonic energy generated by the acoustic assemblies during a treatment exits the apparatus directed toward the group focal zone. The apparatus has a treatment configuration in which the apparatus is positionable relative to the skin of a subject when the apparatus is to be used to perform a treatment on the subject. In the treatment configuration, the emission surface of the acoustic pad is positionable adjacent a surface of the skin of the patient so that at least a portion, and preferably substantially all, of the geometrically focused ultrasonic energy exiting the apparatus directed to the group focal zone exits the apparatus through the emission surface of the acoustic pad. When the acoustic pad is in the treatment configuration, the group focal zone is located within a range of distances distal to the acoustic emission surface, with the range having a lower limit of 0.5 centimeter distal to the acoustic emission surface and an upper limit selected from the group consisting of 10 centimeters, 8 centimeters, 6 centimeters and 5 centimeters distal to the acoustic emission surface. One preferred implementation is for the group focal zone to be located within a range of 0.5 to 5 centimeters distal to the acoustic emission surface. In a preferred implementation, the apparatus is designed so that substantially all of the ultrasonic energy delivered from the apparatus to the group focal zone exits the apparatus through the emission surface of the acoustic pad. An ultrasonic coupling gel is typically used between the emission surface of the acoustic pad and the skin of the patient to increase the energy coupling from the acoustic pad to the tissues of the patient.

The apparatus may be designed to have only a single configuration, i.e., the treatment configuration. Alternatively, the apparatus may be designed to be positionable in multiple different configurations, one of which is the treatment configuration in which the apparatus is disposed to perform a treatment. Other configurations may be as convenient for storage, transportation, maintenance or some other non-treatment purpose. Moreover, the various elements of the apparatus are preferably permanently interconnected in a single device structure, but such is not required. For example, the acoustic assemblies and the acoustic pad, or portions thereof, could be provided in unconnected units that are positionable adjacent to each other in the treatment configuration when the apparatus is to be used for a treatment.

Advantageously, the acoustic assemblies are designed so that when operated each acoustic assembly generates ultrasonic energy at a resonant frequency in a range of 275 KHz to 800 KHz. This is an important aspect of the apparatus which, in combination with other features of the apparatus, permit the apparatus to be used to effectively perform non-invasive ultrasonic treatment in a safe manner, and with substantial soft-tissue destruction within the group focal zone due primarily to positive and negative pressure effects, and without substantial destruction of soft-tissue located outside of the group focal zone. In one preferred implementation, the resonant frequency of each of the acoustic assemblies is within an even narrower range having a lower limit selected from the group consisting of 275 kHz, 300 kHz and 350 kHz and an upper limit selected from the group consisting of 700 kHz 600 kHz and 500 kHz. A particularly preferred range is for the resonant frequency of each of the acoustic assemblies to be within a range of 350 kHz to 500 kHz.

The apparatus may be constructed with a design that permits a compact configuration adapted to be hand-held and hand-manipulated, preferably with one hand, during use to perform a treatment. When adapted to be hand-held during use, the apparatus may be referred to as a "hand piece". When designed as a hand piece, the apparatus should preferably be fitted with a hand-grippable (and preferably single hand-grippable) cover, handle or other structure adapted for gripping.

As noted above, each of the acoustic assemblies preferably has substantially the same resonant frequency and the acoustic assemblies are preferably positioned so that the areas of highest concentrated energy in each individual focal zone intersect and are additive in the group focal zone. In one embodiment, the ultrasonic energy in the individual focal zone of each single acoustic assembly is selected so that it, by itself, is not sufficient to destroy a substantial portion of soft-tissue located within the individual focal zone during a period of time corresponding to a treatment time for treating soft-tissue within the group focal zone. However, the ultrasonic energy in the group focal zone, which is preferably the summing of the energies of the respective individual focal zones from two or more acoustic assemblies, is sufficient to destroy a substantial portion of the soft-tissue during the treatment time. In preferred implementations, the treatment time for a selected location of soft-tissue is shorter in duration than five (5) seconds.

In one enhancement, the summing of ultrasonic energies from the respective acoustic assemblies is accomplished through electrically connecting the individual acoustic assemblies in series, to electrically drive the acoustic assemblies in phase with each other. For enhanced performance, the acoustic assemblies are connected to an electronic controller that has feedback control circuitry directed to maintain a selected amplitude of vibration at the resonant frequency. Because the individual acoustic assemblies vibrate at substantially the same resonant frequency and are electrically driven in phase with each other, the generated ultrasonic energy of each acoustic assembly will also be substantially in phase with the ultrasonic energy of each of the other acoustic assemblies, provided that the individual acoustic assemblies are correctly spaced relative to each other and to the group focal zone. The individual focal zones of each of the acoustic assemblies are preferably positioned so that the areas of highest concentrated energy in the individual focal zones intersect within the group focal zone. In the preferred embodiment, the individual acoustic assemblies are held in fixed relation to each other about a hemi-spherical shape that holds the acoustic assemblies at the same fixed radius of curvature so that the individual focal zones intersect within the group focal zone.

The volume contained within the group focal zone is generally designed to be within a range having an upper limit selected from the group consisting of eight (8) cubic centimeters, six (6) cubic centimeters, four (4) cubic centimeters, two (2) cubic centimeters and one and one-half (1.5) cubic centimeters and a lower limit selected from the group consisting of one-half (0.5) cubic centimeter, three-quarters (0.75) cubic centimeter and one (1) cubic centimeter. Within these parameters, for many applications it is preferred that the volume contained within the group focal zone is two (2) cubic centimeters or smaller, and more preferably approximately one (1) cubic centimeter. The focal length of each acoustic assembly is typically in the range from two (2) centimeters to eight (8) centimeters, and preferably from three (3) to six (6) centimeters. The height of the group focal zone (the maximum dimension of the group focal zone as measured substantially perpendicular to the surface of the skin of a patient when the apparatus is disposed adjacent to the skin in the treatment configuration) is typically in a range having a lower limit selected from the group consisting of one-half (0.5) centimeter, three-quarters (0.75) centimeter or 1 centimeter and an upper limit selected from the group consisting of three (3) centimeters, two (2) centimeters, one and one-half (1.5) centimeters and one (1) centimeter. Within these parameters, for many applications it is preferred that the height of the group focal zone is one and one-half (1.5) centimeters or smaller, and more preferably approximately one (1) centimeter. The height of the group focal zone is also typically smaller, and often substantially smaller, than the focal depth of each of the acoustic assemblies.

The individual acoustic assemblies may be constructed as either a 'bias design' with multiple piezo-electric layers retained in compression, or a 'non-bias design' with a single piezo-electric layer adhesively bonded to an acoustic lens. A bias design incorporates a clamp, compression bolt or other compression-retaining structure to maintain the piezo-electric layers in a state of compressive stress as they vibrate.

The apparatus may be triggered to operate for a predetermined period of time sufficient to cause the destruction of at least a portion of the soft-tissue located within the group focal zone. Alternatively, the apparatus may be triggered to operate continuously as it is moved across the surface of the skin.

Other aspects of the invention provide methods for non-invasively treating subcutaneous soft-tissue of a human or other mammalian subject. The methods are implementable using an apparatus described herein, but the methods of the invention are not limited only to use of such apparatus. In preferred implementations, the soft-tissue being treated is adipose tissue. The methods comprise simultaneously directing two or more geometrically focused beams of ultrasonic energy toward the surface of the skin of the subject, wherein the geometrically focused beams of ultrasonic energy each has a frequency within a range of 275 KHz to 800 KHz and has an individual focal zone, and at least a portion of each of the individual focal zones spatially coincides in a group focal zone located in the soft-tissue within a depth range of below the surface of the skin of the subject, wherein the depth range has a lower limit of 0.5 centimeter below the surface of the skin and an upper limit selected from the group consisting of 10 centimeters, 8 centimeters, 6 centimeters and 5 centimeters below the surface of the skin. One preferred implementation is for the group focal zone to be located within a depth range of 0.5 to 5 centimeters below the surface of the skin. Volumes of soft-tissue treated within the group focal zone are subjected to the simultaneously directing of the geometrically focused beams for a period of time sufficient to cause the destruction of at least a portion, and preferably a substantial portion, of such volumes of soft-tissue within the group focal zone. In one aspect, the invention provides such a method in which the ultrasonic energy of any single geometrically focused beam, by itself, is not sufficient to cause the destruction of a substantial portion of the soft-tissue within the group focal zone during the period of time. In another aspect, the invention provides such a method in which the ultrasound energies of the geometrically focused beams are additive in the group focal zone. In a preferred implementation of a method according to the invention, the ultrasonic energies of the geometrically focused beams are additive in the group focal zone and the ultrasonic energy of any single geometrically focused beam, by itself, is not sufficient to cause the destruction of a substantial portion of the soft-tissue located within the corresponding individual focal zone during the period of time.

Treatment of soft-tissue according to methods of the invention typically comprises a destruction of some or all of the soft-tissue, and particularly adipose tissue. By "destruction" or "destroy" as used herein in relation to soft-tissue, it is meant damage done to the soft-tissue as a result of a non-invasive ultrasound treatment that is to such an extent that the tissue will be resorbed and removed from the treated location by natural biological processes of the body.

The period of time to which soft-tissue within the group focal zone is subjected to the simultaneously directing to effect a treatment is typically of very short duration, often shorter than five (5) seconds. In a preferred implementation, the period of time is no longer than three (3) seconds, and more preferably no longer than one (1) second. Typically, however, the period of time will be longer than 0.01 second, preferably longer than 0.05 second and more preferably longer than 0.1 second. As will be appreciated, the period of time for treatment time will vary depending upon the energy level within the group focal zone and the desired extent of tissue destruction. Also, these periods of time for treatment are in relation to the amount of time that any particular volume of soft-tissue is subjected to the simultaneously directing, i.e., the amount of time that volume of soft-tissue is located within the group focal zone and subjected to the energy in the group focal zone provided by the simultaneously directing of the of the focused beams of ultrasonic energy. For example, performance of a treatment may involve continuous or periodic movement of the focused beams laterally in relation to the surface of the skin, so that during a treatment session the group focal zone moves continuously or periodically to encompass new tissue for treatment. Especially during a treatment involving continuous movement of the group focal zone laterally through soft-tissue, the amount of time that any particular volume of tissue will be located within the group focal zone is dependent upon the speed with which the group focal zone is moved through the soft-tissue. In a preferred implementations of methods of the invention, the period of time for subjecting soft-tissue located within the group focal zone to the simultaneously directing the focused beams of ultrasonic energy is sufficiently long to cause destruction of at least twenty (20) percent, and more preferably at least fifty (50) percent, of that soft-tissue (e.g., of adipose tissue). In a preferred implementation, however, the ultrasonic energy of each geometrically focused beam of ultrasonic energy, by itself, is not sufficient to cause destruction of more than ten (10) percent, more preferably less than five (5) percent, and even more preferably less than one (1) percent of the soft-tissue within the corresponding individual focal zone of that geometrically focused beam.

The geometrically focused beams in the methods of treatment may be generated using any apparatus, although use of an apparatus as described herein is preferred. When using an apparatus as described herein, such use may include any feature or features as described herein for such apparatus or any operation thereof.

During a treatment, soft-tissue is treated within a depth range below the surface of the skin, wherein the depth range has a lower limit of 0.5 centimeter below the surface of the skin and an upper limit selected from the group consisting of 10 centimeters, 8 centimeters, 6 centimeters and 5 centimeters below the surface of the skin. One preferred implementation is for treatment of soft tissue within a depth range of 0.5 to 5 centimeters below the surface of the skin of the subject being treated. A treatment session will typically involve moving the group focal laterally in relation to the surface of the subject's skin to treat different volumes of soft-tissue in a layer of tissue within that depth range. During treatment, the geometrically focused beams of ultrasonic energy will typically be generated by an apparatus located adjacent to the surface of the subject's skin. In one implementation, the apparatus is moved laterally in relation to the surface of the skin to cause movement of the group focal zone through the layer of soft-tissue being treated. The movement of the apparatus may involve continuous translational movement of the apparatus across the surface of the skin, or may involve periodic relocation of the apparatus to new locations on the surface of the skin. Moreover, the simultaneously directing of the focused beams may operate in periodic sequential occurrences, with a rest interval between sequential occurrences, or may operate continuously. Operation of the simultaneously directing in a continuous mode will ordinarily be accompanied by movement of the apparatus in a continuous motion across the skin of the subject, to cause continuous movement of the group focal zone through the subcutaneous layer of soft-tissue being treated. In a preferred implementation, the apparatus is hand-held during treatment operation, and is hand-manipulated to effect movement of the apparatus during the treatment operation. The apparatus may be made to be triggerable for a single short interval, for sequential periodic intervals, or for continuous operation.

The body naturally resorbs or removes the damaged adipose and other tissues over a period of time after the treatment. It is, therefore, more practical and safer to address only a limited volume of tissue in each treatment session and multiple treatment sessions may be required to achieve a final desired result. The time between sessions is preferably sufficiently long that removal of damaged tissue following a prior session is mostly or substantially complete. The number of treatment sessions may be two or three, or potentially more than three depending on the total volume of fatty tissue to be addressed and the volume of tissue treated during each session.

It is, among other desirable attributes, a general object of the present invention to provide an improved ultrasonic apparatus for non-invasive, non-surgical (i.e., non-invasive) or destruction of soft-tissues in a human or animal body.

It is a further object of the present invention to provide an improved non-invasive ultrasonic apparatus for destruction of soft-tissues in a patient, and particularly which maximizes destruction of adipose tissues and minimizes trauma to other tissues such as nerves, blood vessels, and lymph tissues, and thus decreases healing time, decreases patient pain, reduces swelling, and decreases bleeding compared to invasive (surgical) approaches to adipose tissue removal.

It is still a further object of the present invention to provide an improved non-invasive ultrasonic treatment apparatus for destruction of soft-tissues in a patient that rapidly destroys said tissues, thereby reducing the time required to complete a treatment.

It is yet still a further object of the present invention to provide an improved non-invasive ultrasonic apparatus that provides uniform, controllable, and predictable destruction of soft-tissues in a patient and which therefore yields an improved cosmetic result for the patient.

It is yet still a further object of the present invention to provide an improved non-invasive ultrasonic apparatus that provides superior control of the ultrasonic beam energy so that damage to tissues above and below the tissue targeted for treatment is minimized.

DETAILED DESCRIPTION

Figure 1:
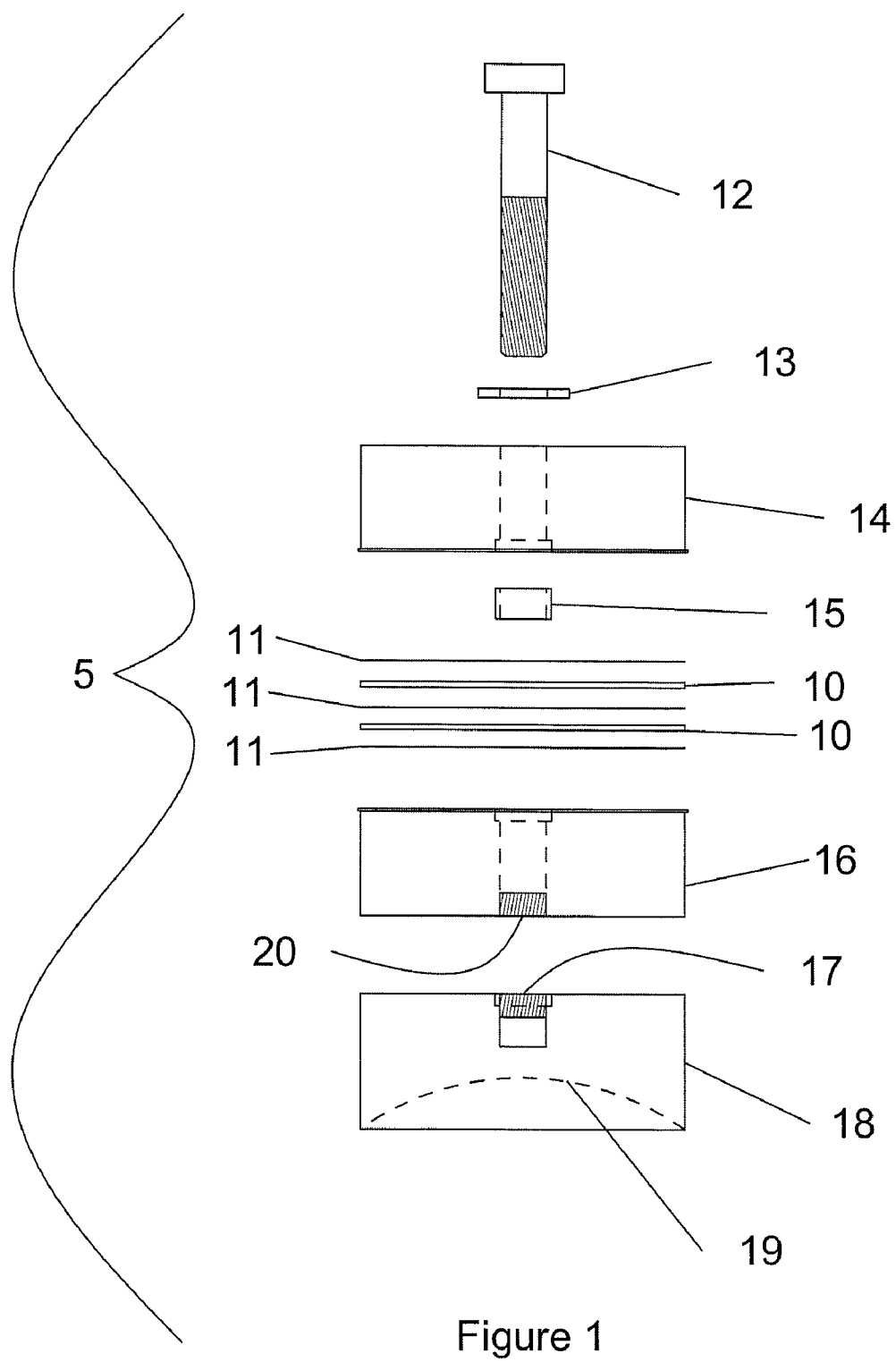
FIG. 1 shows a side view (exploded) of an assembly drawing of an embodiment of a single acoustic assembly of a bias design.

The acoustic assembly of the apparatus may be of any design operable to generate geometrically focused ultrasonic energy. To provide the geometric focusing of the ultrasonic energy, an acoustic assembly may have an ultrasonic transducer that generates ultrasonic energy and an acoustic lens oriented to geometrically focus ultrasonic energy generated by the ultrasonic transducer. By ultrasonic transducer it is meant a structure within the assembly that converts electrical energy into ultrasonic acoustic energy. One embodiment for an acoustic assembly is shown in FIG. 1. FIG. 1 shows a side view of an assembly drawing of a single acoustic assembly 5 having a 'bias design'. 'Bias design' refers to a design approach where piezo-electric ceramic elements are held under compressive stress, or compression bias. This design approach retains the piezo-electric ceramic elements in compression as they vibrate, hence reducing and preferably eliminating tensile stress in the piezo-electric ceramic elements. As shown in FIG. 1, the acoustic assembly 5 includes two piezo-electric ceramic elements 10 located between three electrodes 11 that are electrically connected in parallel. The piezo-electric ceramic elements 11 and the electrodes 10 are alternating layers in a stack, with each ceramic element 10 disposed between two of the electrodes 11. Other numbers of piezo-electric ceramic elements are possible in even multiples such as four (4), (six) (6), etc., which would also require additional electrodes. The piezo-electric ceramic elements are typically made of lead zirconate titanate, commonly referred to as PZT. The preferred PZT materials are Navy Type I (PZT-4) and Navy Type III (PZT-8) due to their generally higher power handling capabilities. The piezo-electric ceramic elements 10 are fabricated into discs with a central hole. The thickness of each such disc is chosen so that the combined thickness of the multiple discs is less than about one-eighth of a wavelength at the chosen resonant frequency for the acoustic assembly 5, although a combined thickness up to ½ of a wavelength at the chosen resonant frequency is functional. The piezo-electric ceramic elements 10 are electrically energized through electrical connection to the electrodes 11 to produce ultrasonic vibrational energy that resonates in the acoustic assembly 5. The electrodes 11 are typically fabricated from thin sheets of conductive metal, typically 0.025 millimeters to 0.125 millimeters thick, depending on the metal chosen. Examples of some metal materials for such electrodes include beryllium copper, aluminum, nickel, and stainless steel. A compression bolt 12 is used to create the compressive bias stress. The compression bolt 12 is sized such that the tensile stress in the bolt does not exceed the rated stress for the bolt size. A washer 13 is used prevent the head of the compression bolt from deforming a back spacer 14. The back spacer 14 is round in shape and fabricated from metal, such as for example aluminum, steel, or titanium. The thickness of the back spacer 14 is selected in cooperation with the other components of the acoustic assembly 5 so that the resonant frequency of the assembled device is a selected value. An insulation sleeve 15 electrically insulates the electrically conductive compression bolt 12 from the inner edges of the electrodes 11 and the piezo-electric ceramic elements 10. A front spacer 16 is round in shape and fabricated from metal, such as for example aluminum, steel, or titanium. As with the back spacer 14, the thickness of the front spacer 16 is selected in cooperation with the other components of the acoustic assembly so that the resonant frequency of the assembled device is the selected value. The front spacer 16 has a threaded portion 17 to engage threads on the compression bolt 12 to retain all components between the head of the bolt 12 and the threaded portion 17 in compression. An acoustic lens 18 is attached, preferably bound (such as with an adhesive), to the front spacer 16. The acoustic lens 18 is round in shape with a concave, spherical surface 19 to create a focusing of the ultrasonic vibrational energy. By spherical surface it is meant that the surface 19 has a curvature corresponding to the curvature of a portion of a surface of a sphere. The acoustic lens 18 may be fabricated from metal such as aluminum, but is preferably fabricated from a polymeric material with a lower acoustic impedance than metal to facilitate improved matching between the acoustic assembly and the tissue of the patient. The acoustic lens 18 has a threaded portion 20 that engages the threads on the compression bolt 12. Adhesive may be placed between the acoustic lens 18 and the front spacer 16 to improve the acoustic coupling between the acoustic lens 18 and the front spacer 16. The stack of piezo-electric ceramic elements 10 and electrodes 11 form the ultrasonic transducer of the acoustic assembly 5 to convert electrical energy into ultrasonic acoustic energy. The acoustic lens 18 is disposed adjacent to the end of the stack to geometrically focus ultrasonic energy from the ultrasonic transducer in the individual focal zone of the acoustic assembly.

Figure 2:
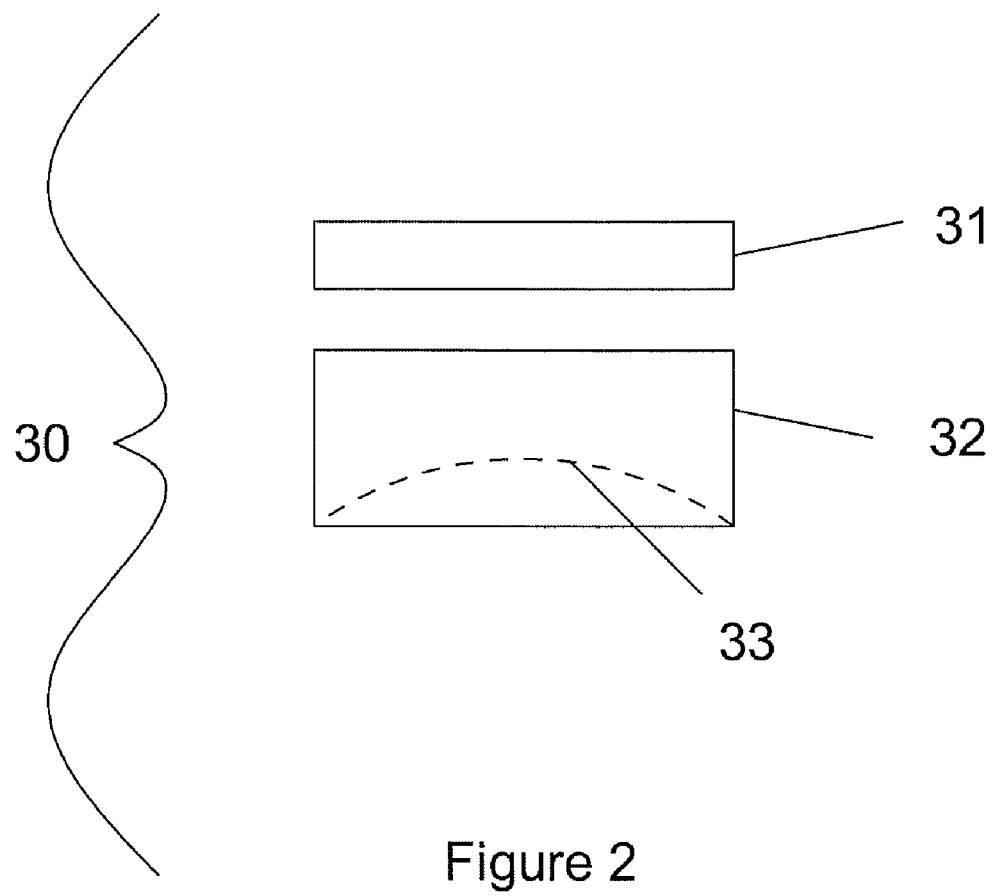
FIG. 2 shows a side view (exploded) of an assembly drawing of an embodiment of a single acoustic assembly of the non-bias design.

Another embodiment for an acoustic assembly is shown in FIG. 2. FIG. 2 shows a side view of an assembly drawing of a single acoustic assembly 30 of a 'non-bias design'. 'Non-bias design' refers to an alternative design approach where the piezo-electric ceramic element is not maintained under compressive stress. As shown in FIG. 2, the acoustic assembly 30 includes a piezo-electric ceramic element 31, which is round in shape and may be fabricated from the piezo-electric ceramic materials, such as those listed above. The piezo-electric ceramic element is electrically energized through electrical connection to electrodes typically coated onto the top and bottom surfaces of the element (not separately shown). The piezo-electric ceramic element 31 is preferably adhesively bonded to an acoustic lens 32. The acoustic lens 32 is round in shape and may be fabricated for example from metals, such as aluminum or titanium, or from appropriate polymers. The preferred material for acoustic lens 32 is aluminum because it possesses an acoustic impedance between the acoustic impedance of piezo-electric ceramic and the acoustic impedance of patient tissue. The acoustic lens 32 has a spherical surface 33 to focus the ultrasonic energy in an individual focal zone for the acoustic assembly 30.

Figure 3:
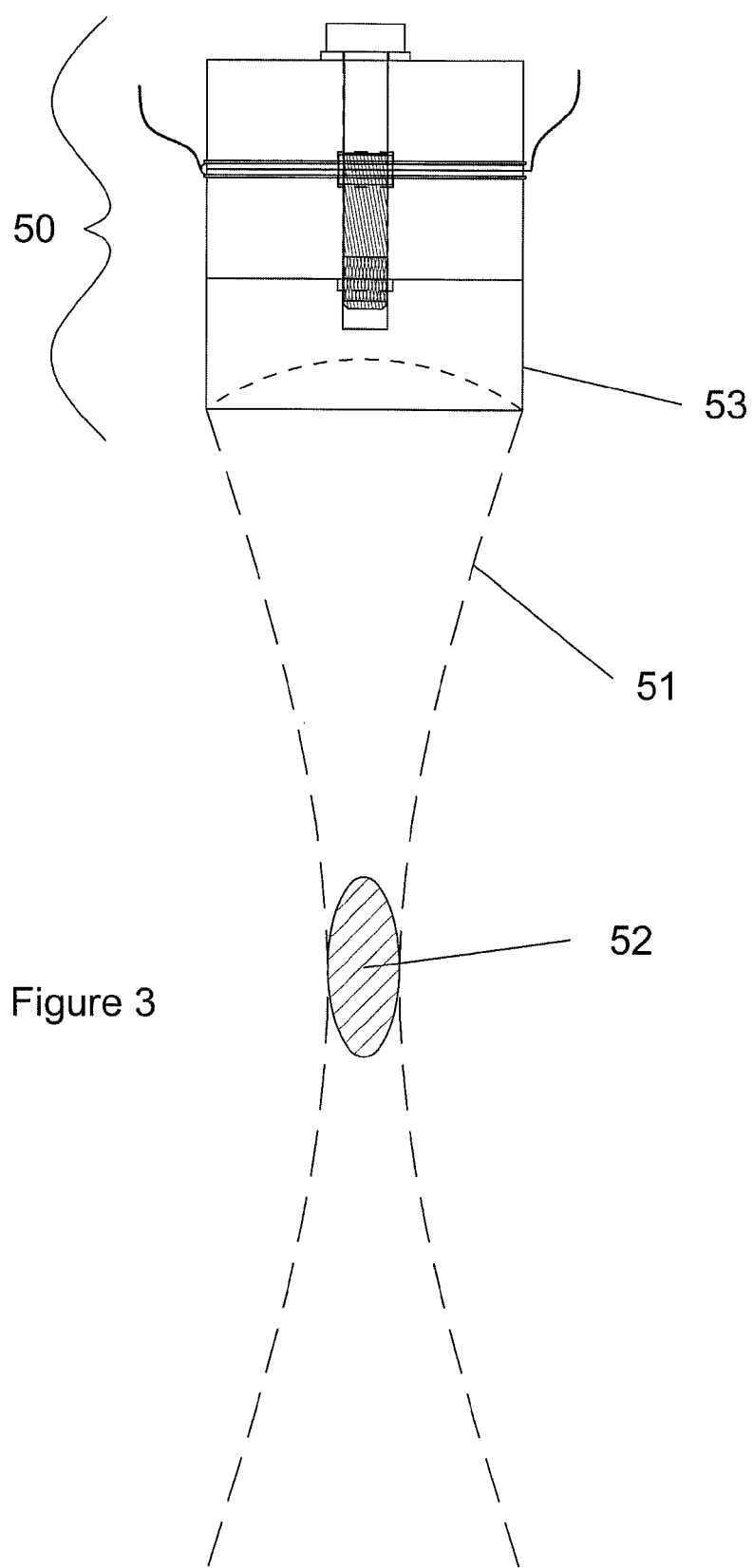
FIG. 3 shows an illustration from the side of an embodiment of a single acoustic assembly of a bias design that is assembled, showing a geometric concentration of generated ultrasonic energy in an individual focal zone distal to a focusing lens.

FIG. 3 illustrates a single acoustic assembly 50 that is assembled (bias design). FIG. 3 also illustrates a beam 51 of ultrasonic energy generated when the acoustic assembly 51 is operated. The beam 51 of ultrasonic energy is geometrically focused by an acoustic lens 53 in an individual focal zone 52 located distal to the acoustic lens 53. The acoustic assembly 50 is of a bias design generally of the type shown in FIG. 1. The same principles of geometric focus also apply, however to non-bias designs, such as for example the one shown in FIG. 2. Geometric concentration of ultrasonic energy refers to focusing a plano-concave acoustic lens, such as acoustic lens 53, as opposed to focusing that can be accomplished between multiple elements in a phased array.

Figure 4:
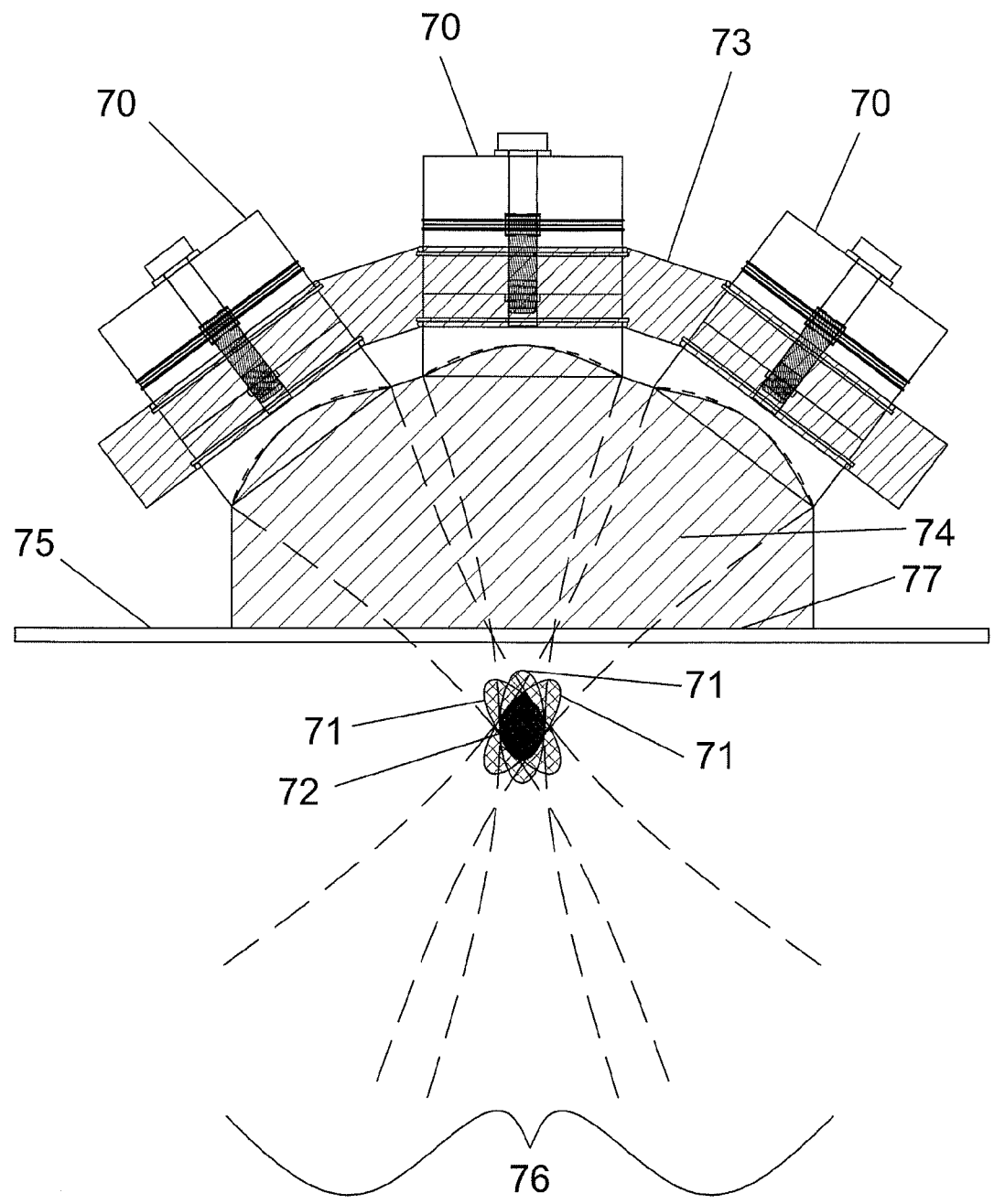
FIG. 4 shows an illustration from the side of an embodiment of an apparatus with three acoustic assemblies of a bias design spatially arranged so that portions of the respective individual focal zones coincide, or intersect, in a group focal zone, located within a depth range of from 0.5 centimeters to 10 centimeters below the surface of a patient's skin.

FIG. 4 illustrates one embodiment of an apparatus including three acoustic assemblies. FIG. 3 shows an apparatus 68 with three acoustic assemblies 70 spatially arranged so that the respective individual focal zones 71 intersect with a summing of ultrasonic energy in a group focal zone 72, the group focal zone 72 being located within a depth range of from 0.5 centimeter to 10 centimeters below the surface of the skin 75 of a patient. This figure shows bias design acoustic assemblies generally of a type as shown in FIGS. 1 and 3. Non-bias design acoustic assemblies, such as for example as shown in FIG. 2, may be used instead. The acoustic assemblies 70 are held in fixed relation to each other by a transducer support 73. Transducer support 73 orients each acoustic assembly 70 so that a substantial portion of each respective individual focal zone 71 coincides to form the group focal zone 72, so that the ultrasonic energy is additive in the group focal zone 72. The apparatus also includes an acoustic pad 74, which provides an acoustic couple for transmitting the ultrasonic energy from the acoustic assemblies 70 to the surface of the skin 75 of a patient. The acoustic pad 74 will generally have an acoustic impedance between the acoustic impedance of acoustic lenses 78 of the acoustic assemblies 70 and the acoustic impedance of soft-tissue below the surface of the skin 75 of the patient. Individual geometrically concentrated beams 76 of ultrasonic energy of each acoustic assembly are represented by dashed lines. The acoustic pad 74 has an acoustic emission surface 77 that contacts the surface of the skin 75 of the patient. Ultrasonic coupling gels or oils may, however, be placed between the acoustic emission surface 77 and the surface of the skin 75 of the patient to improve ultrasonic energy coupling. The group focal zone 72 has a different shape of concentrated ultrasonic energy than the individual focal zones 71. The individual focal zones 71 have a generally ellipsoidal and elongated shape, as shown in FIG. 4, and also in FIG. 3. The additive concentration of energy in the group focal zone 72 has a higher energy density due to the additive effect and a reduced height as compared to the individual focal zones 71, as shown in the figure. This aspect of the group focal zone 72 provides improved control of the energy densities immediately above and below the group focal zone 72, thus improving the protection of tissues above and below the group focal zone.

Figure 5:
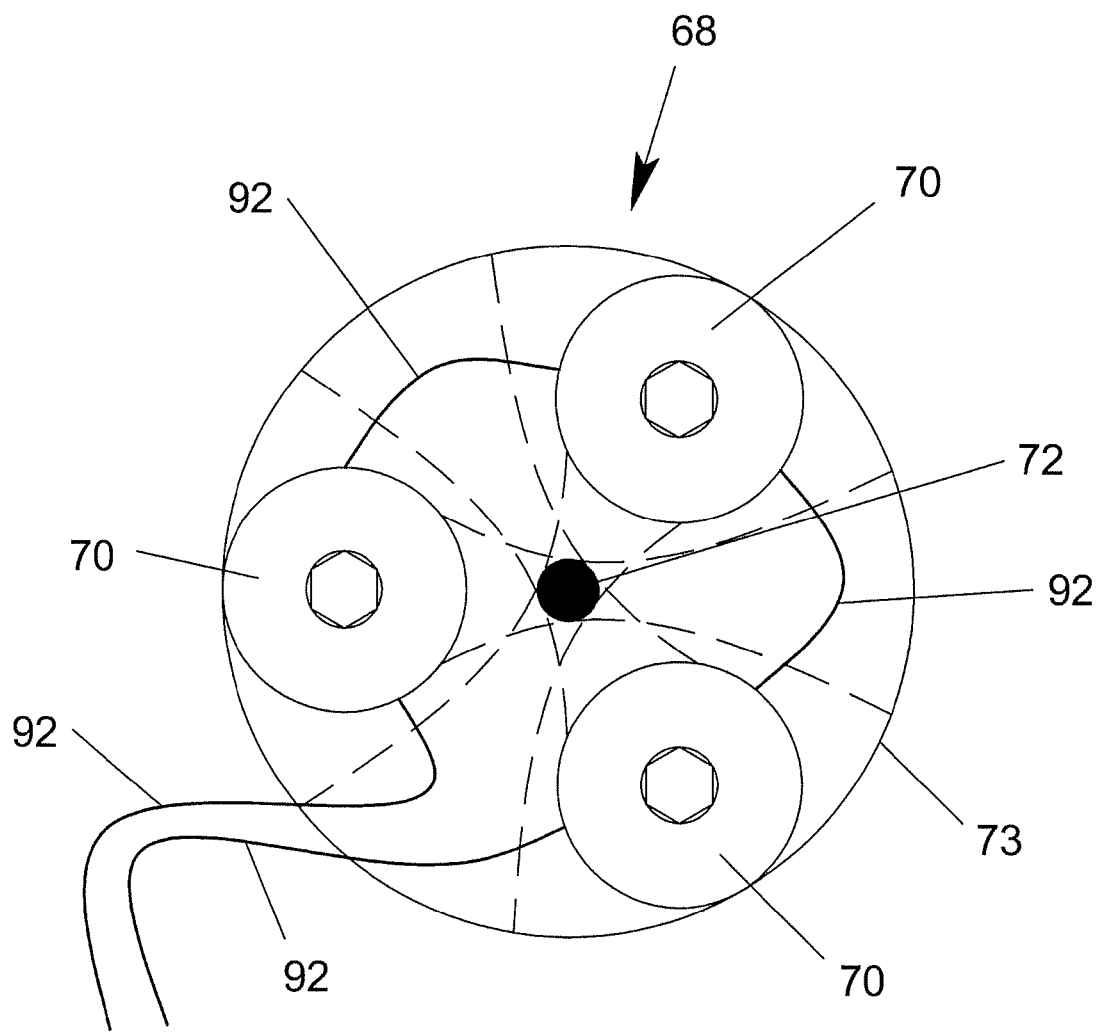
FIG. 5 shows an illustration of the top of the same apparatus as shown in FIG. 4, and showing the group focal zone.

FIG. 5 shows an illustration of the top of the same apparatus 68 as shown in FIG. 4. FIG. 5 shows the arrangement of the three acoustic assemblies 70 spatially arranged and retained in fixed relation by the transducer support 73 so that the respective individual focal zones intersect with a summing of ultrasonic energy in the group focal zone 72. Electrically conductive wires 92 electrically connect the three acoustic assemblies 70 in series. The series connection of the acoustic assemblies assures that acoustic energy is generated in phase for each of the acoustic assemblies. When the acoustic assemblies are spatially arranged as shown in FIG. 4 the summing of acoustic energies is possible in the group focal zone.

Figure 6:
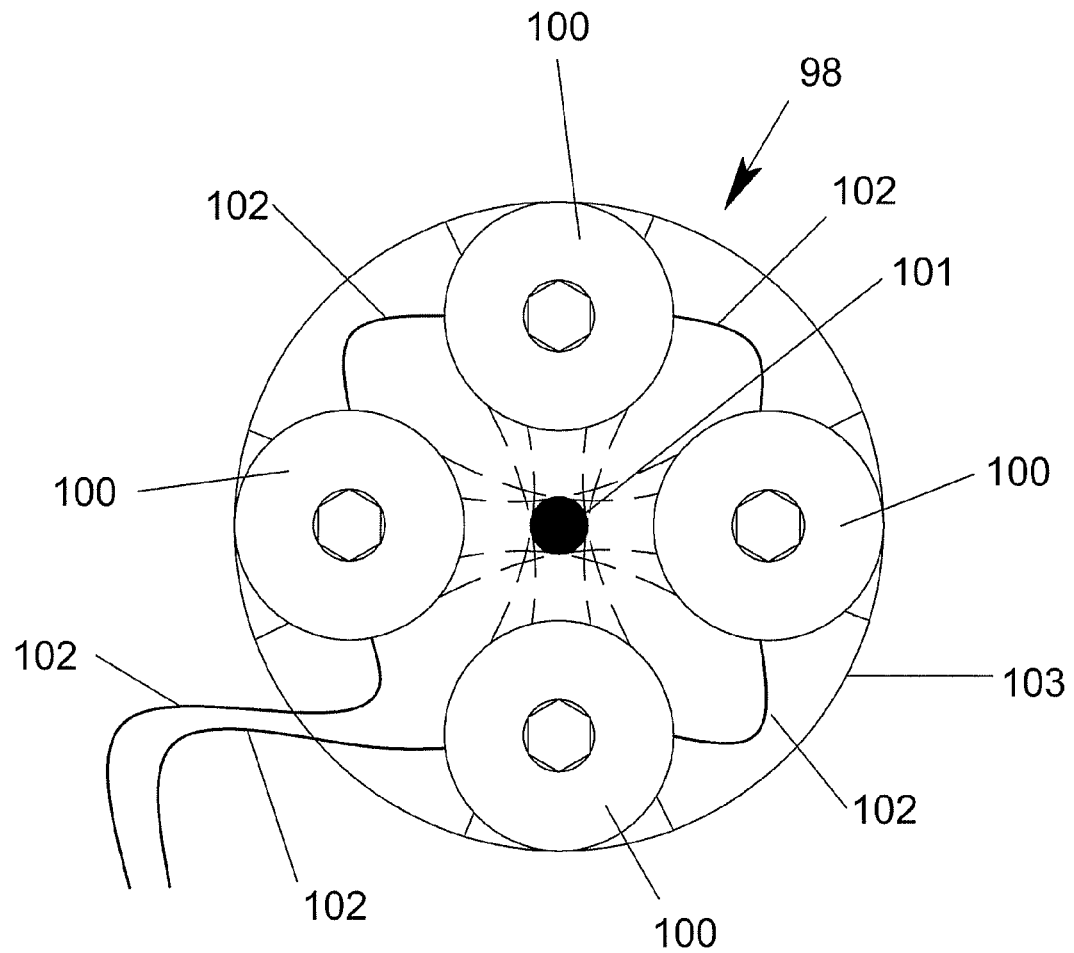
FIG. 6 shows an illustration of the top of and embodiment of an apparatus with an arrangement of four acoustic assemblies spatially arranged so that the respective individual focal zones coincide, or intersect, in a group focal zone.

FIG. 6 is an illustration, viewed from the top, of another embodiment of an apparatus of the invention, generally of a similar design to that shown in FIGS. 4 and 5, but with four acoustic assemblies instead of three. As shown in FIG. 6, an apparatus 98 includes four acoustic assemblies 100, which are spatially arranged so that substantial portions of their respective individual focal zones coincide with a summing of ultrasonic energy in a group focal zone 101. This figure shows bias design acoustic assemblies as shown in FIG. 1. Non-bias design acoustic assemblies, such as for example as shown in FIG. 2, may be used instead. Electrically conductive wires 102 electrically connect the four acoustic assemblies 100 in series. Transducer support 103 holds the acoustic assemblies 100 in fixed relationship to each other with an orientation so that the respective individual focal zones intersect with a summing of ultrasonic energy in the group focal zone 101.

Figure 7:
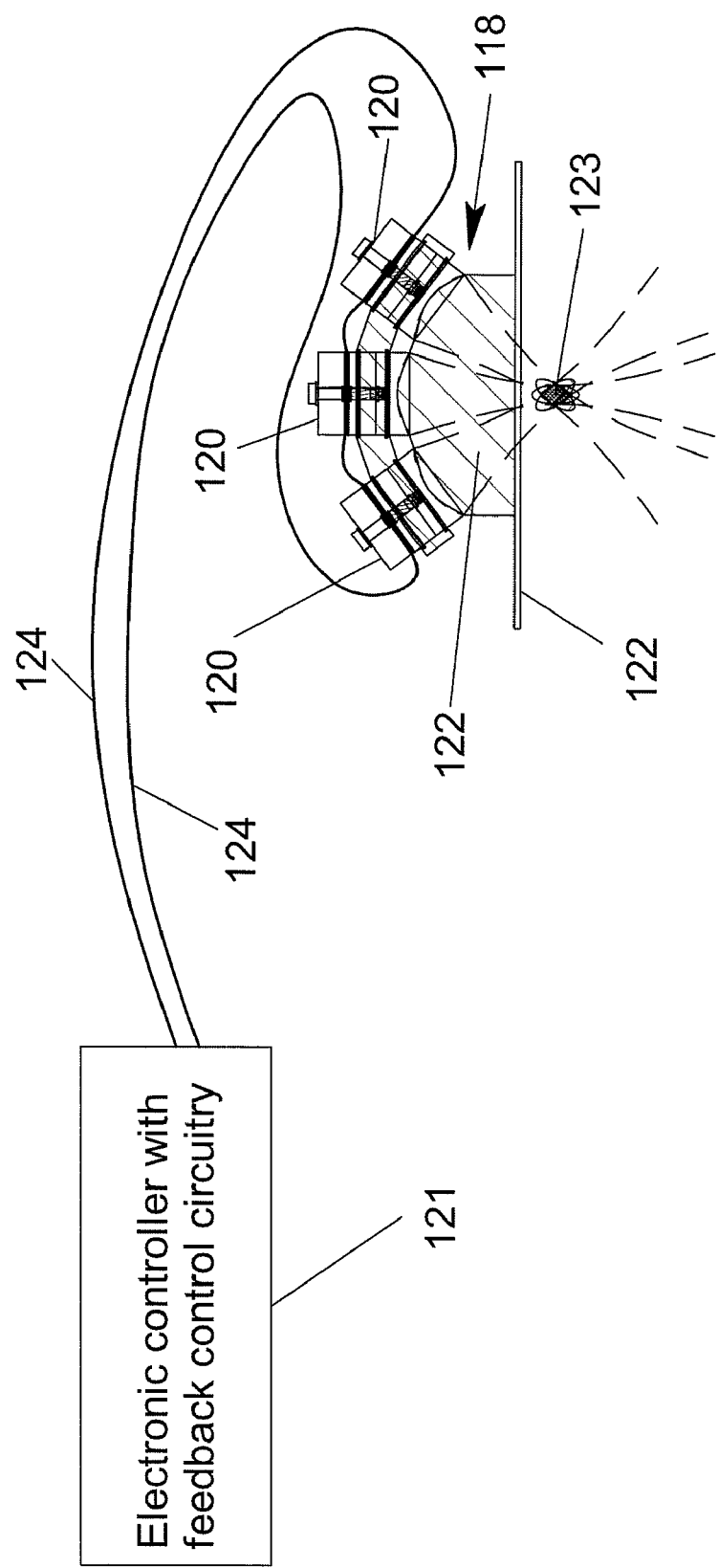
FIG. 7 is a diagrammatic representation of an embodiment of an apparatus with three acoustic assemblies connected to an electronic controller with feedback control circuitry.

FIG. 7 is a diagrammatic representation showing one embodiment of an apparatus 118 including three acoustic assemblies 120 electrically connected in series and electrically connected to electronic controller circuitry with feedback control 121. The apparatus has an acoustic pad 122, to provide an acoustic coupling between acoustic lenses of the acoustic assemblies 120 and skin 125 of a patient, adjacent to which an emission surface 127 of the acoustic pad 122 is disposed. Wires 124 electrically connect the acoustic assemblies 120 to electronic controller 121 comprising feedback control circuitry. Electronic feedback control circuitry in the electronic controller 121 provides electronic feedback control for control of the magnitude of the amplitude of vibration of the acoustic assemblies 120 at the resonant frequency. The electronic feedback control circuitry may be provided by any circuitry providing feedback control that operates to help keep the amplitude of vibration of the acoustic assemblies 120 at a relatively constant value at a predetermined level. One example of a possible electronic feedback control circuit is shown in the schematic diagram in FIG. 8. For purposes of illustration, an apparatus 140 of the invention, for example any of the embodiments as shown in any of FIGS. 4-7 is labeled as "Hand Piece PZT" in FIG. 8.

Figure 8:
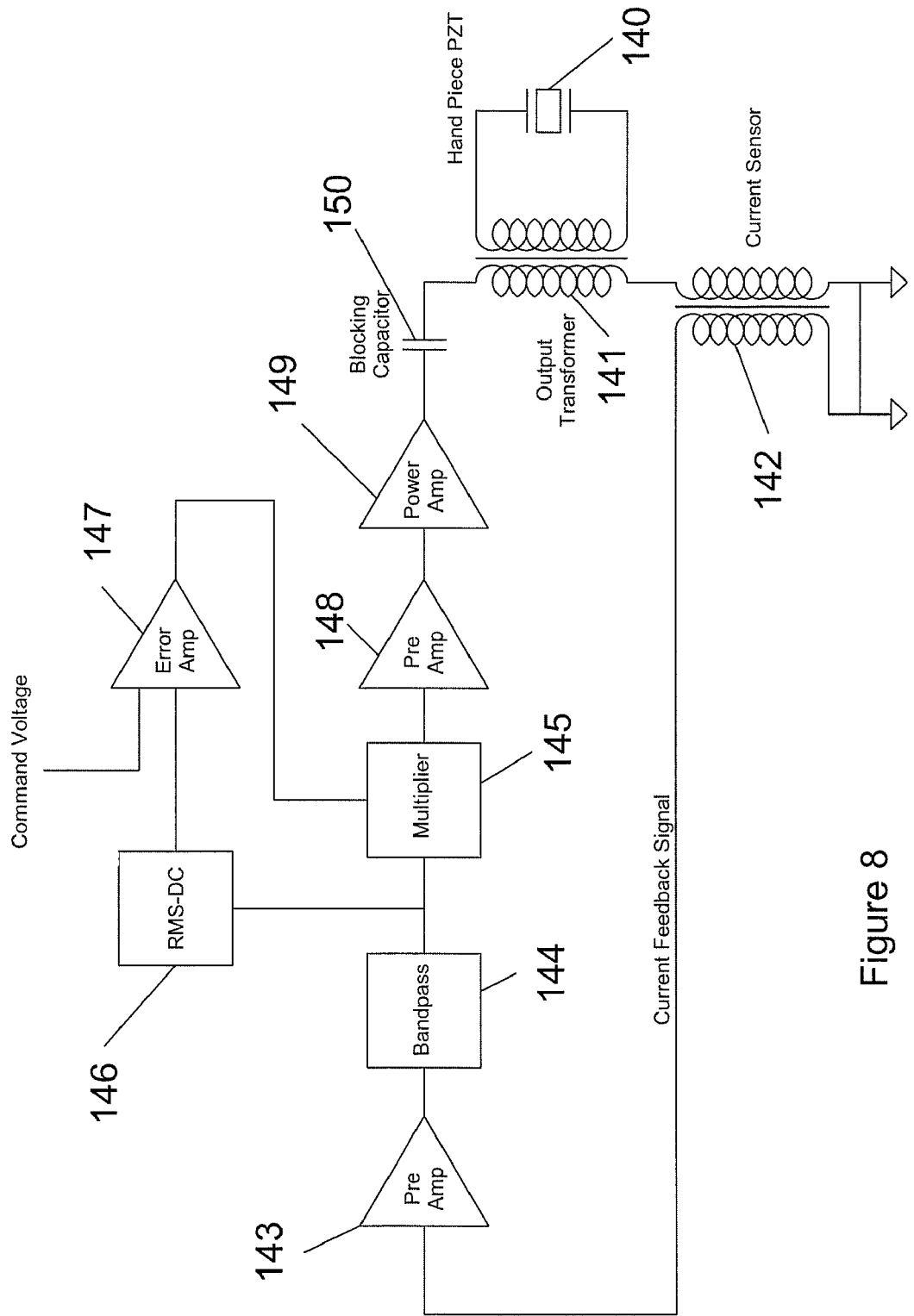
FIG. 8 is a schematic diagram of an embodiment of an electronic control circuit with feedback control.

The apparatus 140 is electrically connected to an output transformer 141. Current sense transformer 142 provides a feedback signal proportional to the current through output transformer 141. Other means of feedback sensing could be used such as voltage across a current sense resistor, phase between the drive voltage and drive current, or from a vibration sensor located in the hand piece. The current sense signal is fed back to a pre-amp 143 that conditions the signal. Bandpass filter 144 selects the resonant frequency and feeds the signal to an analog multiplier circuit 145. The output of the bandpass filter 144 is also passed to a RMS to DC converter circuit 146. An error amplifier 147 compares the output of the RMS to DC converter circuit 146 to a command voltage and provides the second input to the analog multiplier circuit 145. The output of the analog multiplier circuit 145 is conditioned by pre-amp 148 and passed to power amplifier 149. Blocking capacitor 150 eliminates a DC current path through output transformer 141. The circuit shown in FIG. 8 is only one example of possible variation of feedback control circuitry. There are a large number of other possible variations of electronic elements within electronic control circuits that could be used to control and operate the apparatus of the invention comprising multiple acoustic assemblies.

The foregoing discussion of the invention has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are necessarily not technically compatible, and all such combinations are within the scope of the present invention.

The terms "comprise", "include", "have" and "contain", and variations of those terms, as may be used in relation to the presence of a feature, are intended to indicate only that a particular feature is present, and are not intended to limit the presence of other features.

What is claimed is:

1. An electrically powered apparatus for non-invasive ultrasonic treatment of subcutaneous soft-tissue of a human or other mammalian subject, the apparatus comprising:
   at least three simultaneously operable acoustic assemblies retained in fixed relation to each other, the apparatus being configured for operation when connected to an electrical power source to energize the acoustic assemblies and simultaneously generate ultrasonic energy from each said acoustic assembly, wherein:
   (i) each said acoustic assembly generates ultrasonic energy at a resonant frequency in a range of from 275 kHz to 800 kHz;
   (ii) each said acoustic assembly comprises an ultrasonic transducer acoustically coupled with an acoustic lens oriented to produce a geometrically focused beam of ultrasonic energy generated by the ultrasonic transducer;

(iii) the ultrasonic energy of the geometrically focused beam of each said acoustic assembly is focused in an individual focal zone located distal to the apparatus; and (iv) the acoustic assemblies are oriented so that at least a portion of the highest concentrated energy of each said individual focal zone spatially coincides in a group focal zone;

the apparatus being configured for positioning in a treatment configuration relative to a skin of a subject to perform a non-invasive ultrasonic treatment on the subject;

an acoustic pad with an acoustic emission surface that, in the treatment configuration, is configured for positioning adjacent a surface of the skin of the subject through which at least a portion of the ultrasonic energy generated by the acoustic assemblies exits the apparatus directed toward the group focal zone located within a range of from 0.5 centimeter to 10 centimeters distal to the acoustic emission surface;

and wherein:

the apparatus is configured for operation with each said geometrically focused beam, by itself, not being sufficient to cause destruction of a portion of the soft-tissue located within the corresponding individual focal zone of said geometrically focused beam during a treatment; and the acoustic assemblies are electrically connected in series to drive the acoustic assemblies in phase at a resonant frequency, whereby the apparatus is configured for operation with the ultrasonic energies of the geometrically focused beams of the different acoustic assemblies being additive in the group focal zone to produce a larger concentrated ultrasonic energy in the group focal zone with a larger amplitude of vibration than from any one of the acoustic assemblies, with the larger concentrated energy being sufficient to cause destruction of a portion of the soft-tissue within the group focal zone during the treatment due primarily to positive and negative pressure effects caused by the larger amplitude.

2. The apparatus according to claim 1, wherein the resonant frequency of each said acoustic assembly is within a range of 350 kHz to 500 kHz.

3. The apparatus according to claim 1, wherein the volume occupied by the group focal zone is not larger than eight cubic centimeters.

4. The apparatus according to claim 1, wherein at least when the apparatus is in the treatment configuration adjacent to the surface of the skin, the acoustic emission surface is disposed between the acoustic lens and the skin of the subject, the acoustic pad providing an acoustic coupling between each said acoustic lens and the skin of the patient.

5. The apparatus according to claim 4, wherein the acoustic pad is bound to a surface of each said acoustic lens.

6. The apparatus according to claim 4, wherein each said acoustic lens has a focal length in a range of from two to six centimeters.

7. The apparatus according to claim 4, wherein:

each said ultrasonic transducer includes a stack comprising multiple piezo-electric ceramic layers retained in compression; and the acoustic lens is disposed adjacent an end of the stack facing the individual focal zone of the acoustic assembly.

8. The apparatus according to claim 7, wherein the stack comprises multiple electrode layers, each said piezo-electric layer being disposed between two said drive electrode layers.

9. The apparatus according to claim 4, wherein each said acoustic assembly includes a single piezo-electric layer adhesively bonded to the acoustic lens.

10. The apparatus according to claim 1, wherein the acoustic assemblies are electrically connected to electronic feedback control circuitry to provide feedback control to control magnitude of amplitude of vibration of the acoustic assemblies frequency.

11. The apparatus according to claim 1, wherein each said acoustic assembly has a focal length in a range of from two to six centimeters.

12. The apparatus according to claim 1, comprising from three to six of the acoustic assemblies.

13. The apparatus according to claim 1, wherein the apparatus is configured for triggerable operation to cause an actuation of the simultaneous operation of the acoustic assemblies that is automatically limited to lasting for a predetermined period of time, each said actuation being sufficient for the ultrasonic energies generated by the acoustic assemblies to cause destruction of at least a portion of soft-tissue located within the group focal zone during the period of time, wherein the ultrasonic energy generated by each said acoustic assembly is not sufficient, by itself, to cause the destruction of a portion of the soft-tissue within the group focal zone during the period of time.

14. The apparatus according to claim 13, wherein the apparatus is configured for triggerable operation to cause repeated occurrences of the actuation with sequential occurrences of the actuation being automatically separated by a rest interval of fixed duration during which the ultrasonic assemblies are not operated.

15. The apparatus according to claim 1, wherein the apparatus is configured for being hand-held adjacent the surface of the skin during operation of the apparatus to perform the non-invasive ultrasonic treatment.

16. The apparatus according to claim 1, wherein the group focal zone has a height in a range of from 0.5 centimeter to 2 centimeters.

17. The apparatus according to claim 16, wherein the volume occupied by the group focal zone is no larger than four cubic centimeters.

18. The apparatus according to claim 16, wherein the volume occupied by the group focal zone is no larger than two cubic centimeters and the group focal zone has a height in a range of from 0.5 centimeter to 1.5 centimeters.

19. The apparatus according to claim 1, wherein the apparatus is configured so that in the treatment configuration the ultrasonic energy delivered from the apparatus to the group focal zone exits the apparatus through the emission surface of the acoustic pad.

20. The apparatus according to claim 19, wherein in the treatment configuration all of the group focal zone is disposed distal to the apparatus.

* * * * *